United States Patent
Auer et al.

(10) Patent No.: US 6,867,329 B2
(45) Date of Patent: Mar. 15, 2005

(54) WASTE WATER TREATMENT IN A METHOD FOR PRODUCING FORMIC ACID WHICH IS FREE OF WATER

(75) Inventors: Heinz Auer, Neulussheim (DE); Bernd Bessling, Grosse Ille, MI (US); Hans Hammer, Mannheim (DE); Hans Hasse, Kaiserslautern (DE); Friedrich Sauer, Obersülzen (DE); Maximilian Vicari, Limburgerhof (DE); Till Adrian, Bobenheim-Roxheim (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 10 days.

(21) Appl. No.: 10/181,455

(22) PCT Filed: Jan. 12, 2001

(86) PCT No.: PCT/EP01/00346

§ 371 (c)(1),
(2), (4) Date: Jul. 18, 2002

(87) PCT Pub. No.: WO01/55069

PCT Pub. Date: Aug. 2, 2001

(65) Prior Publication Data

US 2003/0036664 A1 Feb. 20, 2003

(30) Foreign Application Priority Data

Jan. 24, 2000 (DE) .......................................... 100 02 794

(51) Int. Cl.$^7$ .............................................. C07C 53/02

(52) U.S. Cl. ....................... 562/609; 562/606; 562/607; 562/608

(58) Field of Search ................................. 562/512, 609

(56) References Cited

U.S. PATENT DOCUMENTS 4,326,073 A * 4/1982 Wolf et al. .................. 562/609

FOREIGN PATENT DOCUMENTS

EP           17 866          10/1980

OTHER PUBLICATIONS

Derwent Abstract of Japan XP–002175587.
Ullmanns Encyclopedia of Ind.Chem.5thEd.,vol. A12,16–24.
Ullmanns Encyclopedia of Ind.Chem.4thEd.vol. 4,365–366.

* cited by examiner

Primary Examiner—Johann R Richter
Assistant Examiner—Karl Puttlitz
(74) Attorney, Agent, or Firm—Keil & Weinkauf

(57) ABSTRACT

The invention relates to a process for obtaining anhydrous or substantially anhydrous formic acid, in which firstly aqueous formic acid is prepared by hydrolysis of methyl formate and is freed from water in the subsequent work-up. The process has the special feature that steam, which is employed for the hydrolysis of methyl formate and for heating a distillation column serving for work-up, is also used as stripping steam for waste-water stripping. The stripped waste water is produced during work-up.

7 Claims, 4 Drawing Sheets

Figure 1:
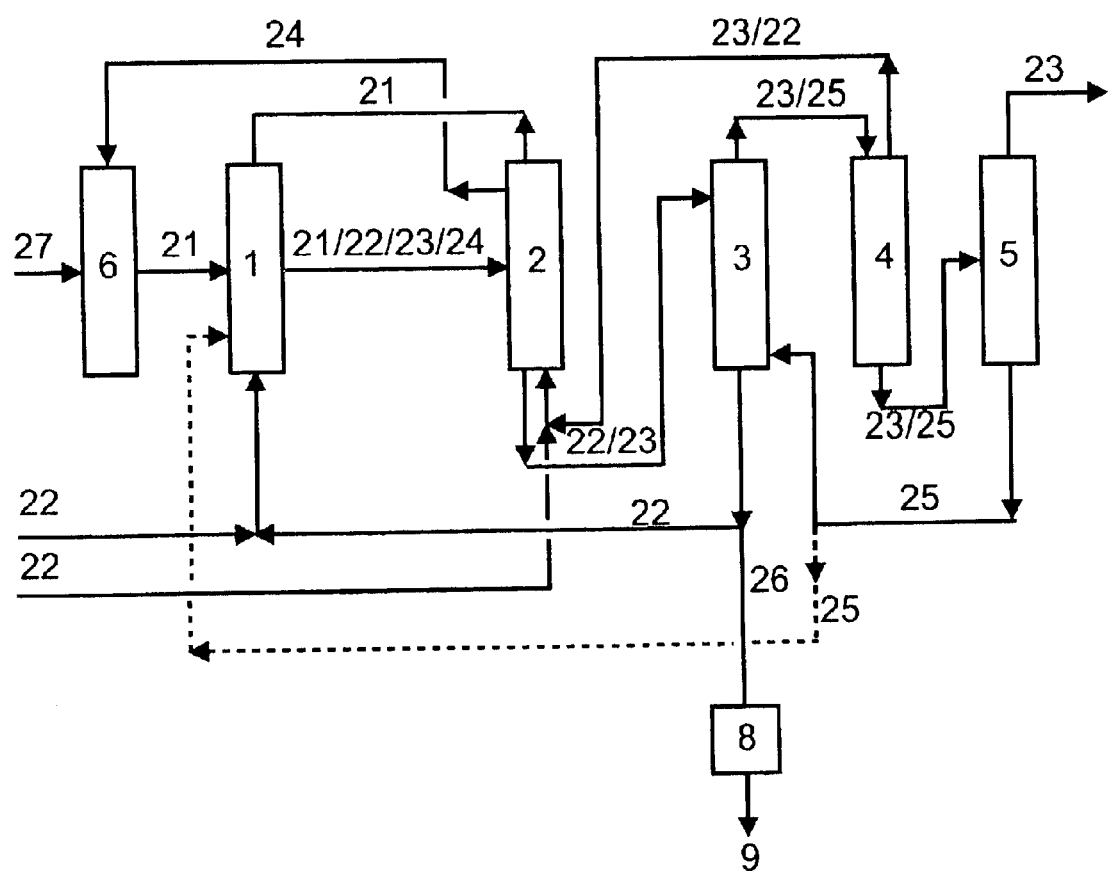

WASTE WATER TREATMENT IN A METHOD FOR PRODUCING FORMIC ACID WHICH IS FREE OF WATER

The present invention relates to an apparatus and a process for obtaining anhydrous or substantially anhydrous formic acid, and to the use of a stream of steam in this process.

TECHNICAL FIELD

"Ullmanns Encyklopädie der technischen Chemie" [Ullmann's Encyclopedia of Industrial Chemistry], 4$^{th}$ Edition, Volume 7, page 365, discloses that formic acid can be prepared by acidolysis of formamide using sulfuric acid. However, this process has the disadvantage that stoichiometric amounts of ammonium sulfate are obtained as an unavoidable product.

Another way of preparing formic acid consists in the hydrolysis of methyl formate, which is synthesized from methanol and carbon monoxide. This synthesis is based on the following equations:

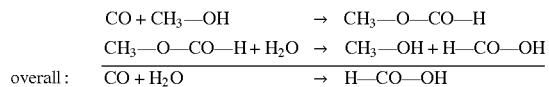

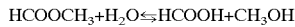

The hydrolysis of methyl formate described in "Ullmanns Encyklopädie der technischen Chemie" [Ullmann's Encyclopedia of Industrial Chemistry], 4$^{th}$ Edition, Volume 7, page 366

$$HCOOCH_3 + H_2O \leftrightarrows HCOOH + CH_3OH$$

has the disadvantage of an unfavorable position of the hydrolysis equilibrium. A shift in the equilibrium by removing the desired process products by distillation is not possible since methyl formate (boiling point 32° C.) boils significantly lower than methanol (boiling point 65° C.) and formic acid (boiling point 101° C.). Anhydrous formic acid cannot easily be obtained from the resultant aqueous formic acid solution by distillation since it forms an azeotrope with water. The difficulty thus consists in obtaining anhydrous formic acid from the methyl formate hydrolysis mixture.

BACKGROUND OF THE ART

A process described in EP-B-0 017 866 which comprises steps a) to g) enables the preparation of anhydrous formic acid starting from methyl formate. Anhydrous formic acid is obtained here if a) methyl formate is subjected to hydrolysis, b) methanol and excess methyl formate are distilled off from the resultant hydrolysis mixture, c) the bottom product from the distillation (b), which comprises formic acid and water, is extracted in a liquid-liquid extraction with an extractant which principally takes up the formic acid, d) the resultant extract phase, comprising formic acid, extractant and some of the water, is subjected to distillation, e) the top product obtained in this distillation, which comprises water and some of the formic acid, is fed back into the lower part of the distillation column in step (b), f) the bottom product from distillation step (d), which predominantly comprises extractant and formic acid, is separated into anhydrous formic acid and the extractant by distillation, and g) the extractant leaving step (f) is fed back into the process.

In this process, it is particularly advantageous h) to carry out distillation steps (b) and (d) in a single column, i) to introduce the water necessary for the hydrolysis in the form of steam into the lower part of the column provided for carrying out step (b), k) to employ methyl formate and water in the hydrolysis (a) in a molar ratio of from 1:2 to 1:10, and/or l) to employ, as extractant, a carboxamide of the general formula I

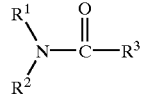

where the radicals $R^1$ and $R^2$ are alkyl, cycloalkyl, aryl or aralkyl groups, or $R^1$ and $R^2$ jointly, together with the N atom, form a hetero-cyclic 5- or 6-membered ring, and only one of the radicals is an aryl group, and where $R^3$ is hydrogen or a $C_1$–$C_4$-alkyl group.

Steps (a) to (i) of the above-described process are explained in greater detail below.

Step (a)

The hydrolysis is usually carried out at a temperature in the range from 80 to 150° C.

Step (b)

The distillation of the hydrolysis mixture can in principle be carried out at any desired pressure, preferably from 0.5 to 2 bar. In general, working under atmospheric pressure is advisable. In this case, the temperature at the bottom of the column is about 110° C. and the temperature at the top of the column is from about 30 to 40° C. The hydrolysis mixture is advantageously added at a temperature in the range from 80 to 150° C., and the methanol is preferably removed in liquid form at a temperature of from 55 to 65° C. Satisfactory separation of the mixture into methyl formate and methanol on the one hand and aqueous formic acid on the other hand is possible even using a distillation column which has 25 theoretical plates (the theoretical number of plates is preferably from 35 to 45). Any design can be used for the column intended for step (b), but a sieve plate or packed column is particularly recommended.

Step (c)

The liquid-liquid extraction of the formic acid from its aqueous solution by means of an extractant is preferably carried out at atmospheric pressure and a temperature of from 60 to 120° C., in particular from 70 to 90° C., in countercurrent. Depending on the type of extractant, extraction devices having from 1 to 12 theoretical separation stages are generally required. Suitable extraction devices for this purpose are in particular liquid-liquid extraction columns. In most cases, satisfactory results are achieved using from 4 to 6 theoretical separation stages.

The choice of extractant is not limited. Particularly suitable extractants are carboxamides of the general formula I given above. Extractants of this type are, in particular, N,N-di-n-butylformamide and in addition N,N-di-n-butylacetamide, N-methyl-N-2-heptylformamide, N-n-butyl-N-2-ethylhexylformamide, N-n-butyl-N-cyclohexylformamide and N-ethylformanilide, and mixtures of these compounds. Further suitable extractants are, inter alia, diisopropyl ether, methyl isobutyl ketone, ethyl acetate, tributyl phosphate and butanediol formate.

Step (d)

The extract phase is separated by distillation in an appropriate distillation device into a liquid phase, which generally comprises predominantly formic acid and extractant, and a vapor phase predominantly comprising water and small amounts of formic acid. This is an extractive distillation. The bottom temperature is preferably from 140 to 180° C. A satisfactory separation effect is generally achieved from 5 theoretical plates.

Step (e)

The formic acid/water mixture is generally recycled in vapor form.

Steps (f) and (g)

The distillation device (usually in the form of a column) for carrying out step (f) is advantageously operated under reduced pressure—from about 50 to 300 mbar and correspondingly low head temperatures—from about 30 to 60° C.

Step (h)

This variant of the process relates to steps (b) and (d). The distillation devices for carrying out steps (b) and (d) are arranged in an overall distillation device. The distillation devices here are generally in the form of columns.

Step (i)

In this step, water required for the hydrolysis is provided in the form of steam.

It has proven particularly advantageous to introduce the water necessary for the hydrolysis in the form of steam into the lower part of the distillation device proposed for carrying out step b). Thermal energy in the form of steam is thereby introduced into the process simultaneously with the water which is anyway needed for the hydrolysis. Through the introduction of the steam, sufficient energy is introduced into the distillation device so that the corresponding still evaporator can be designed correspondingly smaller, since less energy has to be introduced through the still evaporator.

It is necessary to remove from the process some of the aqueous phase formed during the liquid-liquid extraction of the formic acid in order to provide an exit for low-volatility secondary components (for example salts). Otherwise, low-volatility secondary components would accumulate in the process, having an adverse effect on the product quality. However, the aqueous phase exiting the extraction device for carrying out the liquid-liquid extraction still contains small amounts of valuable products, in particular formic acid and extractant. These products must not enter the waste water, since the extractants employed are generally of low biodegradability. In order to treat the waste water formed and to recover the valuable products, a multicolumn adsorber circuit is generally used, whose purchase and operation is very expensive, with regeneration of the adsorbent generally being particularly expensive. The adsorbent employed is generally activated carbon.

DISCLOSURE OF THE INVENTION

It is an object of the present invention to provide a process which ensures the recovery of the valuable products from the waste water leaving the extraction device, with the waste water being freed from the valuable products and any other impurities so thoroughly that further treatment of the waste water is no longer necessary. The process should be practical to carry out and economically attractive.

We have found that this object is achieved by a process for obtaining anhydrous or substantially anhydrous formic acid in which i) methyl formate is subjected to hydrolysis, ii) methanol and excess methyl formate are distilled off from the resultant hydrolysis mixture in a distillation device, and steam is fed into the lower part of this distillation device, iii) the bottom product from distillation ii), comprising formic acid and water, is extracted in a liquid-liquid extraction with an extractant which principally takes up the formic acid, and some of the aqueous phase formed in the liquid-liquid extraction is removed from the process as waste water, iv) the resultant extract phase, comprising formic acid, extractant and some of the water, is subjected to distillation, v) the top product obtained in this distillation, which comprises water and some of the formic acid, is fed back into the lower part of the distillation device in step ii), vi) the bottom product from distillation step iv), which comprises predominantly extractant and formic acid, is separated by distillation into anhydrous or substantially anhydrous formic acid and the extractant, and vii) the extractant leaving step vi) is fed back into the process, which comprises employing steam introduced into the distillation device provided for carrying out step (ii), before introduction into this distillation device, as stripping steam for waste-water stripping of the waste water removed from the process in step iii).

The term "substantially anhydrous formic acid" is taken to mean formic acid which contains a maximum of 30%, preferably a maximum of 15%, of water. The term "steam" is taken to mean gaseous water, where the latter may also contain liquid constituents and other components (apart from water).

The process according to the invention is particularly economical since the steam which is required anyway for the process is additionally employed for waste-water treatments. The process saves energy, requires low investment costs and is simply to carry out. The waste water can be cleaned so effectively by the process that the waste water can subsequently be fed directly into a treatment plant. In addition, valuable products from the process are recovered and recycled.

MODE(S) FOR CARRYING OUT THE INVENTION

In a preferred embodiment of the invention, the extractant employed is a carboxamide of the general formula I

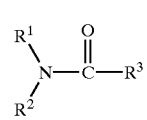

(I)

where the radicals $R^1$ and $R^2$ are alkyl, cycloalkyl, aryl or aralkyl groups, or $R^1$ and $R^2$ jointly, together with the N atom, form a heterocyclic 5- or 6-membered ring, and only one of the radicals is an aryl group, and where $R^3$ is hydrogen or a $C_1$–$C_4$-alkyl group. Particularly preferred extractants are N,N-di-n-butylformamide, N,N-di-n-butylacetamide, N-methyl-N-2-heptylformamide, N-n-butyl-N-2-ethylhexylformamide, N-n-butyl-N-cyclohexylformamide and/or N-ethylformanilide. The extractant employed can be a single extractant or an extractant mixture.

In a preferred embodiment of the invention, steps (ii) and (iv) are carried out in a single distillation device.

The steam employed as stripping steam generally has a temperature of from 110 to 200° C., preferably from 140° to 180° C. The temperature at which the stripping steam is introduced into the distillation device is usually lower.

The invention also relates to the use of a steam stream in the process described above. In this case, the steam stream is firstly used as stripping steam stream for waste-water stripping and subsequently as starting-material stream for providing water for the hydrolysis of methyl formate.

The invention also relates to an apparatus for carrying out the process described above. This comprises α) a synthesis reactor,
β) a hydrolysis reactor,
χ) a distillation device for carrying out step ii),
δ) a distillation device for carrying out step iv),
ε) an extraction device,
ϕ) a distillation device for carrying out step vi), and
γ) a waste-water stripping device.

The term "synthesis reactor" is taken to mean a device in which firstly the synthesis of methyl formate is carried out (usually in a corresponding reactor) and in which secondly, if desired, separation of the resultant hydrolysis mixture is carried out (usually in a distillation device downstream of the reactor). The hydrolysis reactor in which the hydrolysis of methyl formate is carried out can have any desired design. The distillation devices employed are preferably distillation columns. The extraction device is generally in the form of a liquid-liquid extraction column. The waste-water stripping device employed is generally a stripping column. This stripping column usually has from 3 to 20, preferably from 5 to 10, thermodynamic separation stages.

In a preferred embodiment of the invention, the distillation device for carrying out step ii) and the distillation device for carrying out step iv) are arranged in a single distillation device. The latter is generally in the form of a distillation column.

Figure 2:
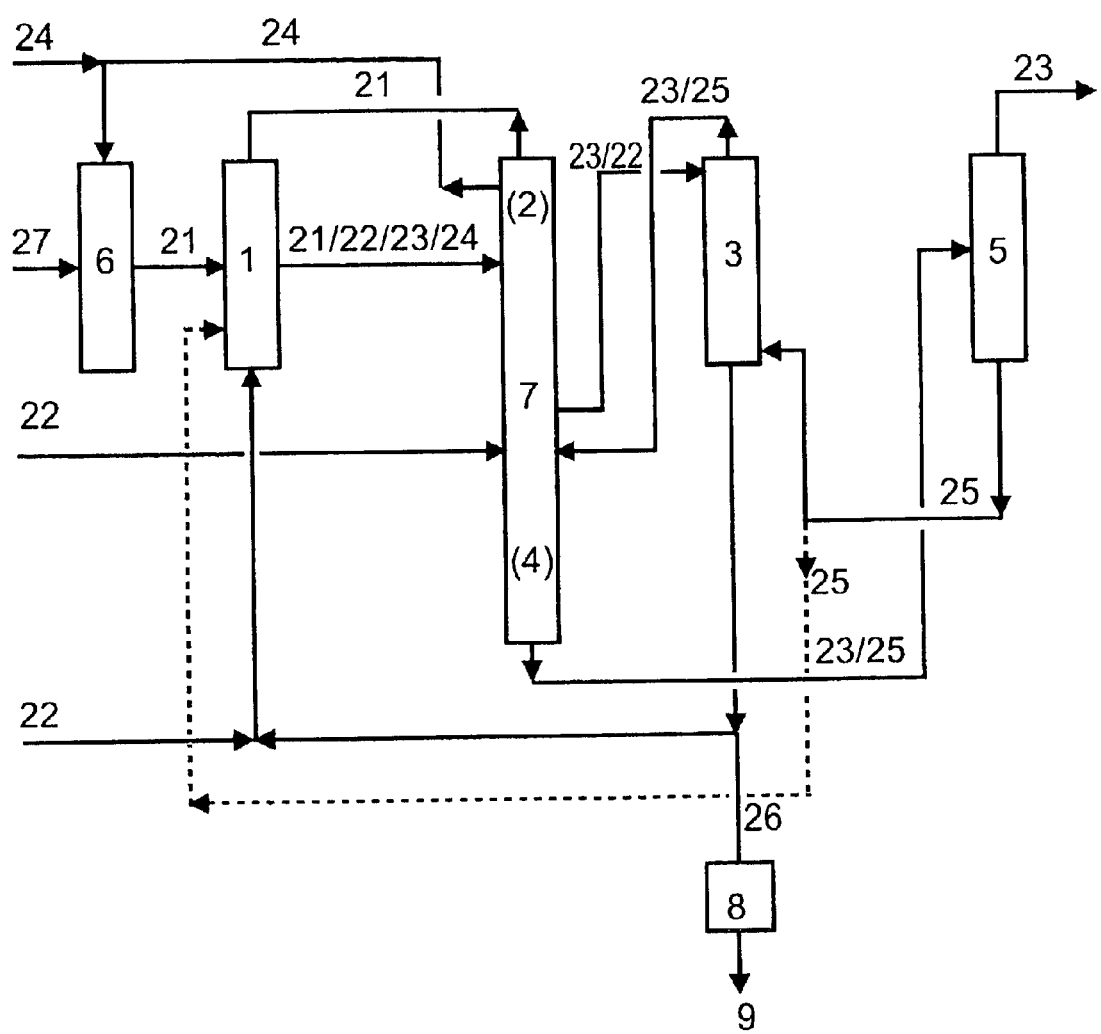
Figure 3:
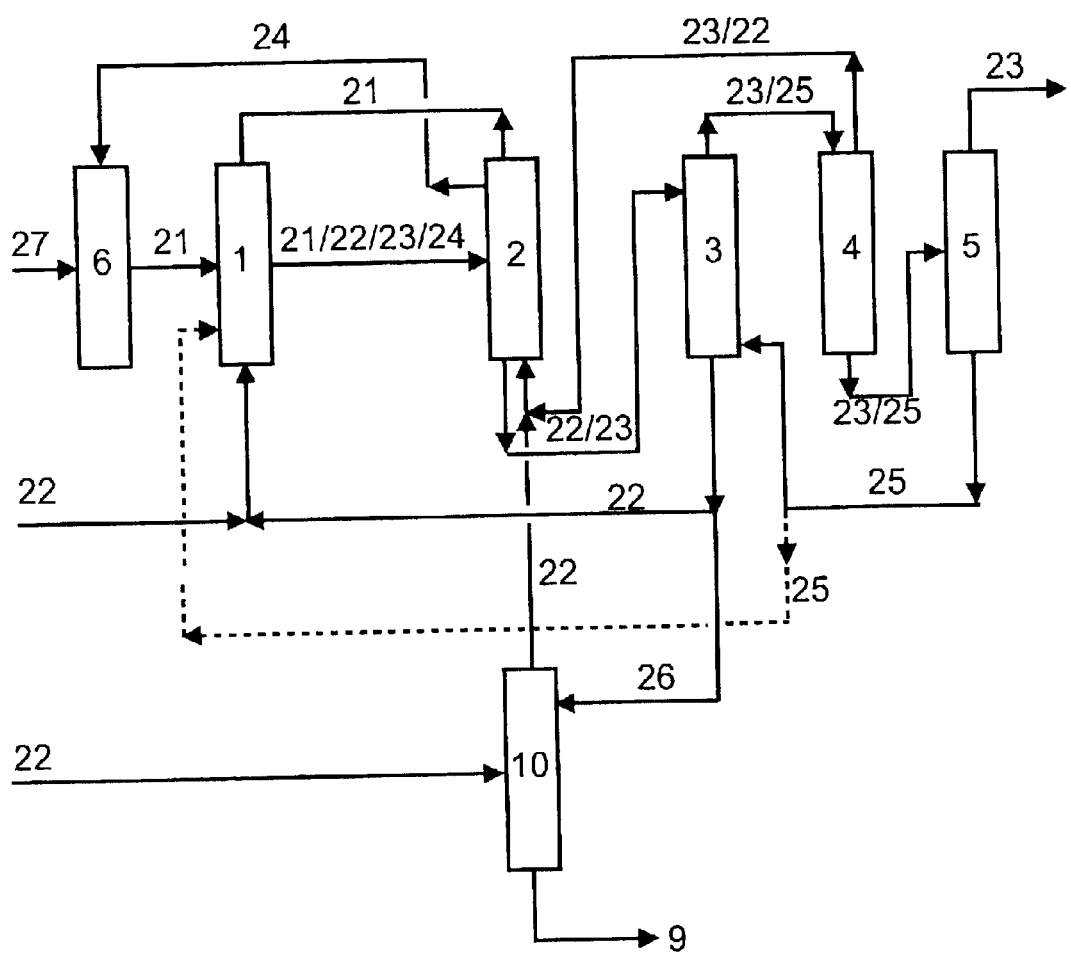
Figure 4:
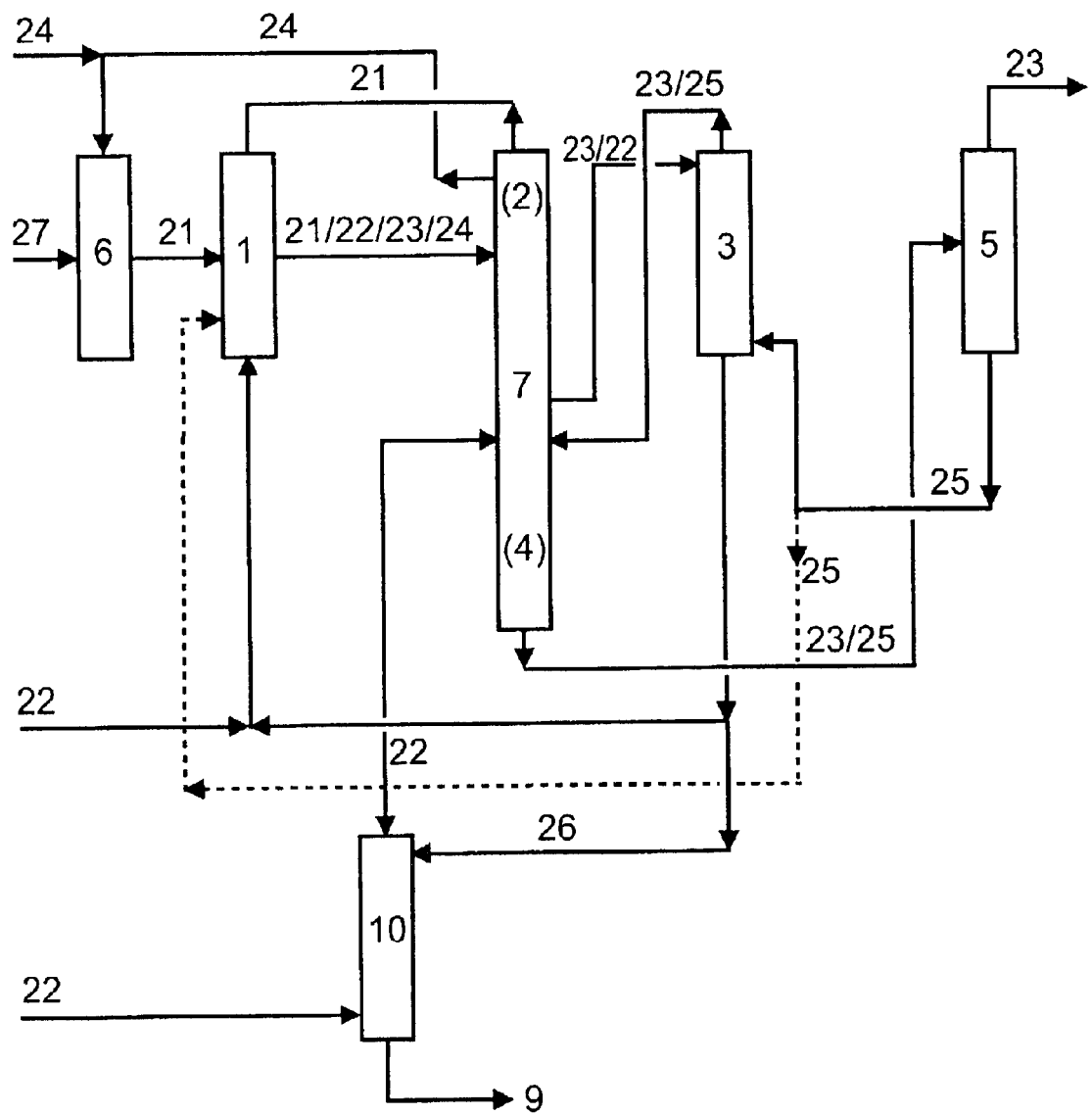

The attached drawing shows in FIG. 1 and in FIG. 2 diagrams of plants for carrying out prior-art processes for the preparation of anhydrous formic acid, and in FIG. 3 and in FIG. 4 diagrams of plants for carrying out the process according to the invention.

The numbers entered above, alongside or below the connecting lines are intended to give an indication of the components which have the greatest proportion in the corresponding streams. However, since these components may vary, these reference numerals can only serve as guide values. 21 here denotes methyl formate, 22 denotes water, 23 denotes formic acid, 24 denotes methanol, 25 denotes extractant, 26 denotes waste water and 27 denotes carbon monoxide.

It is common to the plants shown in FIG. 1 and FIG. 2 for carrying out a prior-art process and the plants shown in FIG. 3 and FIG. 4 for carrying out the process according to the invention that they have a synthesis reactor 6, a hydrolysis reactor 1, a distillation device 2 for carrying out step (ii), a distillation device 4 for carrying out step (iv), an extraction device 3 and a distillation device 5 for carrying out step (vi). The distillation devices 2, 4 here may be arranged in a common distillation device 7.

In contrast to the plants shown in FIG. 1 and FIG. 2, the plants for carrying out the process according to the invention (FIG. 3 and FIG. 4) contain a waste-water stripping device 10. The cleaned waste water is fed therefrom into the treatment plant 9. The plants shown in FIG. 1 and FIG. 2 for carrying out the prior-art process contain an adsorber device 8 instead of the waste-water stripping device 10.

The invention will be explained in greater detail below with reference to a working example.

EXAMPLE

The illustrative experiment is carried out in a plant shown diagrammatically in FIG. 4. The extractant used is N,N-di-n-butylformamide. 5.3 kg of aqueous formic acid are prepared continuously. About 400 g/h of waste water are produced in the process. The waste water is stripped in a stripping column using about 1 kg/h of steam. All the extractant is removed from the waste water. The pilot-plant column used for the stripping has a diameter of 30 mm and is fitted with 30 bubble-cap plates. The results of the experiment are shown in Table 1 below.

TABLE 1

|  | Waste water (uncleaned) | Waste water (cleaned) | Stripping stream (unloaded) | Stripping steam (loaded) |
|---|---|---|---|---|
| Amount produced in the process, kg/h | 0.375 | 0.385 | 1.052 | 1.042 |
| Water proportion, % by weight | 98.25 | 99.86 | 100 | 99.42 |
| Extractant proportion, % by weight | 0.76 | 0 | 0 | 0.27 |
| Formic acid proportion, % by weight | 0.99 | 0.14 | 0 | 0.30 |
| Temperature,° C. | 110 | 115 | 160 | 114 |

Table 1 shows that the process according to the invention enables the extractant N,N-di-n-butylformamide to be removed completely and formic acid to be removed substantially from the waste water.

We claim:

1. A process for obtaining anhydrous or substantially anhydrous formic acid, in which i) methyl formate is subjected to hydrolysis, ii) methanol and excess methyl formate are distilled off from the resultant hydrolysis mixture in a distillation device, and steam is fed to the lower part of this distillation device, iii) the bottom product from distillation ii), comprising formic acid and water, is extracted in a liquid-liquid extraction with an extractant which principally takes up the formic acid, and some of the aqueous phase formed in the liquid-liquid extraction is removed from the process as waste-water, iv) the resultant extract phase, comprising formic acid, extractant and some of the water, is subjected to distillation, v) the top product obtained in this distillation which comprises water and some of the formic acid, is fed back into the lower part of the distillation device in step ii), vi) the bottom product from distillation step iv) which comprises predominantly extractant and formic acid, is separated by distillation into anhydrous or substantially anhydrous formic acid and the extractant, and vii) the extractant leaving step vi) is fed back into the process, which process comprises employing steam firstly as stripping steam for waste-water stripping of the waste water removed from the process in step iii), and subsequently introducing the steam employed for stripping into the distillation device provided for carrying out step ii).

2. A process as claimed in claim 1, wherein the extractant is a carboxamide of the general formula I

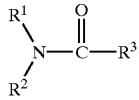
(I)

wherein
R$^1$ is alkyl, cycloalkyl, aryl or aralkyl, and
R$^2$ is alkyl, cycloalkyl or aralkyl, or
R$^1$ and R$^2$ jointly, together with the N atom, form a heterocyclic 5- or 6-membered ring, and
R$^3$ is hydrogen or a C$_1$–C$_4$-alkyl group.

3. A process as claimed in claim 1, wherein the extractant is selected from the group consisting of N,N-di-n-butylformamide, N,N-di-n-butylacetamide, N-methyl-N-2-heptylformamide, N-n-butyl-N-2-ethylhexylformamide, N-n-butyl-N-cyclohexyl-formamide and N-ethylformanilide.

4. A process as claimed in claim 1, wherein steps ii) and iv) are carried out in a single distillation device.

5. A process as claimed in claim 1, wherein the steam employed as stripping steam has a temperature of from 110 to 200° C.

6. A process as claimed in claim 5, wherein the steam employed as stripping steam has a temperature of from 140 to 180° C.

7. A method of applying a steam stream in a process as claimed in claim 1 firstly as stripping steam stream for waste-water stripping and subsequently as starting material stream for providing water for the hydrolysis of methyl formate.

* * * * *